United States Patent [19]
Turner et al.

[11] Patent Number: 5,851,945
[45] Date of Patent: Dec. 22, 1998

[54] OLEFIN POLYMERIZATION CATALYST COMPOSITIONS COMPRISING GROUP 5 TRANSITION METAL COMPOUNDS STABILIZED IN THEIR HIGHEST METAL OXIDATION STATE

[75] Inventors: Howard William Turner; Vincent John Murphy, both of Cupertino, Calif.

[73] Assignee: Exxon Chemical Patents Inc., Houston, Tex.

[21] Appl. No.: 798,412

[22] Filed: Feb. 7, 1997

[51] Int. Cl.$^6$ .............................. B01J 31/00; B01J 37/00; C08F 4/02; C08F 4/60
[52] U.S. Cl. ........................... 502/103; 502/117; 502/124; 502/128; 556/42; 556/43; 526/134; 526/172
[58] Field of Search ..................................... 502/103, 117

[56] References Cited

U.S. PATENT DOCUMENTS

| | | | |
|---|---|---|---|
| 3,052,660 | 9/1962 | Osgan | 502/103 |
| 3,222,333 | 12/1965 | Duck et al. | 502/103 |
| 3,655,583 | 4/1972 | Yamamoto et al. | 502/103 |
| 3,700,710 | 10/1972 | Mottus et al. | 502/103 |
| 4,294,947 | 10/1981 | Doerk et al. | 502/103 |
| 4,508,842 | 4/1985 | Beran et al. | 502/112 |
| 5,017,714 | 5/1991 | Welborn, Jr. et al. | 556/12 |
| 5,036,034 | 7/1991 | Ewen | 502/117 |
| 5,057,475 | 10/1991 | Canich et al. | 502/104 |
| 5,086,023 | 2/1992 | Smith | 502/103 |
| 5,122,493 | 6/1992 | Saba et al. | 502/103 |
| 5,198,399 | 3/1993 | Hoff et al. | 502/117 |
| 5,278,119 | 1/1994 | Turner et al. | 502/103 |
| 5,318,935 | 6/1994 | Canich et al. | 502/117 |
| 5,324,800 | 6/1994 | Welborn, Jr. et al. | 526/103 |
| 5,384,299 | 1/1995 | Turner et al. | 502/103 |
| 5,405,924 | 4/1995 | Kelsey | 502/103 |
| 5,416,053 | 5/1995 | Bai et al. | 502/103 |
| 5,434,116 | 7/1995 | Sone et al. | 502/103 |
| 5,502,124 | 3/1996 | Crowther et al. | 526/160 |
| 5,504,049 | 4/1996 | Crowther et al. | 502/117 |
| 5,670,439 | 9/1997 | Winslow et al. | 502/103 |
| 5,688,733 | 11/1997 | Renkema et al. | 502/103 |
| 5,707,913 | 1/1998 | Schlund et al. | 502/103 |

FOREIGN PATENT DOCUMENTS

| | | | |
|---|---|---|---|
| 0129 368 A1 | 12/1984 | European Pat. Off. . | |
| 0 532 098 A1 | 3/1993 | European Pat. Off. . | |
| 0 641 804 A2 | 3/1995 | European Pat. Off. . | |
| 2 256 695 | 5/1974 | Germany | 502/117 |
| 49-21236 | 5/1974 | Japan | 502/117 |
| WO 92/00333 | 1/1992 | WIPO . | |

OTHER PUBLICATIONS

D.M.T. Chan et al., NATO ASI Ser., Ser. C, vol. 231 (Surf. Organomet. Chem.: Mol. Approaches Surf. Catal.), pp. 187–196. 1988.

"Stable Alkylvanadium(V) Compounds Containing Bulky Imido and Amido Ligands", Horton, et al, Organometallics, vol. 9, pp. 2207–2209 (1990).

I.M. Thomas, Can. J. Chem., vol. 39, pp. 1386–1388 1961.

D.C. Bradley, I.M. Thomas, Can. J. Chem., vol. 40, pp. 1355–1360 1962.

W. Nugent, B. Haymore, Coord. Chem. Rev., vol. 31, pp. 123–175 Feb. 1980.

R. Schrock et al., J. Am. Chem. Soc., vol. 100, No. 11, pp. 3359–3370 May 1978.

C.D. Wood et al., J. Am. Chem.Soc., vol. 101, No. 12, pp. 3210–3222 Jun. 1979.

S. Rocklage et al., J. Am. Chem. Soc., vol. 102, pp. 7808–7809 1980.

S. Rocklage et al., J. Am. Chem. Soc., vol. 104, pp. 3077–3081 1982.

H.C.L. Abbenhuis et al., J. Am. Chem. Soc., vol. 114, pp. 9773–9781 1992.

D.C. Bradley et al., J. Chem. Soc. (A), pp. 980–984 1969.

W. Nugent et al., J. Chem. Soc. Chem. Comm., pp. 579–580 1978.

W. Nugent et al., J. Chem. Soc. Chem. Comm., pp. 342–343 1979.

(List continued on next page.)

*Primary Examiner*—Mark L. Bell
*Assistant Examiner*—J. Pasterizyk
*Attorney, Agent, or Firm*—William G. Muller; Anthony R. Chi

[57] ABSTRACT

The invention addresses Group 5 metal compounds suitable as polymerization catalysts characterized by comprising one Group 15 element polyanionic ancillary ligand and three single or multidentate univalent ligands comprising Group 14–16 elements bound to the Group 5 metal, but excluding cyclopentadienyl ligands. The invention Group 5 metal compounds can be generically represented by the chemical symbols (1) [RJ]MR'$_3$, and (2) [(RJ)Zn(Q)]MR'$_2$ where M is a Group 5 transition metal, preferably vanadium; J is a Group 15 heteroatom ligand covalently bound to M, preferably nitrogen; R is a substituted or unsubstituted aryl, hydrocarbyl or organometalloid group covalently bound to J; each R' is, independently, a uninegative ligand, e.g., substituted or unsubstituted aryl, substituted or unsubstituted linear or cyclic hydrocarbyl, silyl, hydride or substituted or unsubstituted organometalloid group; Q is a univalent single or multidentate ancillary ligand comprising at least one Group 14–16 element covalently bound to M; and, Z is an optional covalent bridging group linking R and Q, comprising at least one Group 14–16 element, n=1 when X is covalently linked to R and n=0 when Q is not covalently linked to R. Catalyst activation can be accomplished with standard metallocene catalyst activators. Olefin polymerization is exemplified.

8 Claims, No Drawings

OTHER PUBLICATIONS

H. Burger et al., Monat. Chem., vol. 95, pp. 292–302 1964.

K. Birdwhistell et al., Organometallics, vol. 12, pp. 1023–1025 1993.

J. Strahle et al., Z. anorg. allg. Chem., vol. 338, pp. 287–298 1965.

A.–F. Shihada, Z. anorg. allg. Chem., vol. 408, pp. 9–14 1974.

"Alkylation and Reductive Dimerization of Half–Sandwich Imido Vanadium Dichlorides," JK. F. Buijink, et al, Journal of Organometallic Chem. 497 (1995) 161–170.

"tert–Butylimino–cyclopentadienyl– alkylvanadium(V-)–Verbindungen Darstellung und NMR–spektroskopische Untersuchungen," F. Preuss, et al, Journal of Zeitschrift Für Naturforschung B, 45B (1990) 191–198.

"Complexes of (arylimido)vanadium(V). Synthetic, Structural, Spectroscopic, and Theoretical Studies of V (Ntol)Cl$_3$ and Derivatives," D. D. Devore, et al, Journal of Amer. Chem. Soc., vol. 109, (1987) 7408–7416.

"Synthesis, Structure, and Olefin Polymerization Activity of Vanadium (V) Catalysts Stabilized by Imido and Hydrotris(pyrazolyl)borato Ligands", Kress, et al, Organometallics vol. 14, pp. 2627–2629 (1995).

OLEFIN POLYMERIZATION CATALYST COMPOSITIONS COMPRISING GROUP 5 TRANSITION METAL COMPOUNDS STABILIZED IN THEIR HIGHEST METAL OXIDATION STATE

TECHNICAL FIELD

This invention relates to organometallic compounds comprising a Group 15 polyanionic ancillary ligand covalently bound to a Group 5 metal center, particularly those suitable for catalysis of olefin polymerization.

BACKGROUND OF THE INVENTION

Coordination polymerization of olefinically unsaturated monomers is well known and has led to the great proliferation of thermoplastic compositions of matter from olefins, such as polyethylene, polypropylene, and ethylene propylene rubber. Early pioneers utilized the early transition metal compounds, particularly those of the Group 4 metals, with such activators as aluminum alkyl compounds. Later developments extended this work to bulky ancillary ligand-containing (e.g., n5-cyclopentadienyl) transition metal compounds ("metallocenes") with activators such as alkyl alumoxanes. Representative work addressing polymer molecular weight effects of substituted mono and bis metallocene compounds is described in EP-A 0 129 368 and its counterpart U.S. Pat. No. 5,324,800. Hetero-atom containing monocyclopentadienyl metallocene compounds are described in U.S. Pat. No. 5,057,475 and silicon bridged biscyclopentadienyl metallocene catalysts are described in U.S. Pat. No. 5,017,714. Recent developments have shown the effectiveness of ionic catalysts comprised of activated metallocene cations stabilized by compatible noncoordinating anions, see for example U.S. Pat. Nos. 5,278,119 and 5,384,299 and WO 92/00333. Each of which is incorporated by reference for purposes of U.S. patent practice.

Transition metal polymerization catalyst systems from Group 5–10 metals wherein the active transition metal center is in a high oxidation state and stabilized by low coordination number polyanionic ancillary ligand systems are described in U.S. Pat. No. 5,502,124 and its divisional U.S. Pat. No. 5,504,049. Suitable low coordination number polyanionic ancillary ligands include both bulky imides and carbolides. Such are said to be suitable alone or in combination with conventional monoanionic ancillary ligands, such as cyclopentadienyl derivatives. Examples 2 and 8 illustrate Group 5 metal catalyst compounds comprising, respectively, (cyclopentadienyl)vanadium(p-tolylimido) dichloride and (cyclopentadienyl)niobium(2,6-diisopropyl-phenylimido) di-methyl. Olefin polymerization catalysts from Group 5 or 6 metal imido complexes are also described in EP 0 641 804. The Group 5 metal complexes include one imido ligand and a monoanionic organic group containing a cyclopentadienyl nucleus. Example 1 illustrates the preparation of (cyclopentadienyl)vanadium (p-tolylimido) dichloride and the Tables on pages 7–9 illustrate polymerization using it. These documents are incorporated by reference for purposes of U.S. patent practice.

Effective olefin polymerization catalysts based upon vanadium alkyl complexes in which the metal center is stabilized in its highest oxidation state are elusive since there are no well established procedures for the synthesis of such compounds. Difficulties associated with the synthesis of vanadium alkyls in which the metal center is stabilized in its highest oxidation state are well documented. See for example, Buijink, J. J. Organomet. Chem 1995, 497, 161–170, Devore, D. D. J. Am. Chem. Soc., 1987, 109, 7408–7416 and other references well known to those skilled in the art.

It would therefore be desirable to provide vanadium alkyl complexes in which the vanadium metal center is stabilized in its highest oxidation state by (a) a low coordination number polyanionic ligand and (b) and suitable additional ancillary ligands.

INVENTION DISCLOSURE

This invention is directed to Group 5 metal compounds, preferably vanadium, suitable for activation as polymerization catalysts and characterized by comprising one polyanionic ancillary ligand and three single or multidentate uninegative ligands, excluding cyclopentadienyl ligands. The polyanionic ancillary ligand will comprise a Group 15 element covalently bound to the Group 5 metal and the uninegative ligands will comprise Group 14–16 elements as single or multidentate ligands bound to the Group 5 metal. The invention includes a polymerization process characterized by comprising contacting one or more monomers polymerizable by coordination or carbocationic polymerization under suitable polymerization conditions with these catalyst compositions.

BEST MODE AND EXAMPLES OF THE INVENTION

The invention Group 5 metal compounds described above can be generically represented by the following symbols:

(1) [RJ]MR'$_3$, and
(2) [(RJ)Zn(Q)]MR'$_2$ where M is a Group 5 metal; J is a Group 15 heteroatom ligand covalently bound to M; R is a substituted or unsubstituted aryl, hydrocarbyl or organometalloid group covalently bound to J, preferably substituted or unsubstituted aryl or alicyclic hydrocarbyl; each R' is, independently, a uninegative ligand, e.g., substituted or unsubstituted aryl, substituted or unsubstituted linear or cyclic hydrocarbyl, silyl, hydride or substituted or unsubstituted organometalloid group, additionally any two R' maybe joined to form a metallocycle; Q is a univalent single or multidentate ancillary ligand comprising at least one Group 14–16 element covalently bound to M; and, Z is an optional covalent bridging group linking R and Q, comprising at least one Group 14–16 element, n=1 when Q is covalently linked to R and n=0 when Q is not covalently linked to R. The term "substituted" means that one or more hydrogen atoms on the hydrocarbyl, aryl or organometalloid group is replaced by a C$_1$–C$_{20}$ hydrocarbyl radical or any of an aryl radical, a halide radical, a phosphido radical, an alkoxide or aryloxide radical (preferably having from one twenty carbon atoms), or any other radical containing a Lewis acidic or basic functionality.

The Group 5 metal compounds of the invention having one polyanionic ancillary ligand and three univalent single or multidentate ligands can be represented by the figures below:

(I)

-continued

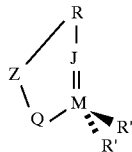 (II)

wherein each of the labeled substituents are as defined above. Suitable single dentate ligands Q include those in the group consisting of aryloxides or alkoxides [—OR$^1$], siloxides [—OSiR$^{1hd\ 3}$], thiols [—SR$^1$], amides [—NR$^1_2$], and phosphides [—PR$^1_2$], where R can be any member within the group defined above for R'. Suitable multidentate ligands are represented by the bidentate carboxylates [—O$_2$CR$^1$], carboxythiolates [—S$_2$CR$^1$], triflates [—O$_3$SR$^1$], acetylacetates [$\eta^2$—R$^1$COCR$^1$COR$^1$], amidates [$\eta^2$—R$^1$NCR$^1$NR$^1$], Group 15 or 16 ortho-substituted pyridines (illustration (a)), Group 15 or 16 substituted hydrocarbyls (illustration (b)), Group 15 or 16 substituted aryls (illustration (c)),

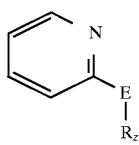 (a)

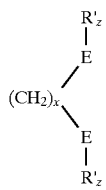 (b)

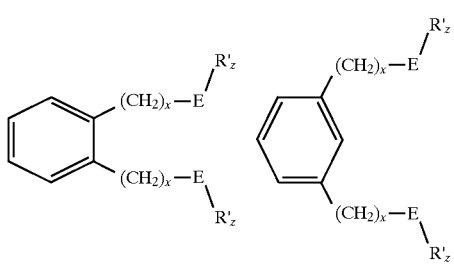 (c)

where x=0–6, each x is selected independently, and E is independently a Group 15 element (in which case z may be 1 or 2) or a Group 16 element (in which case z may be 0 or 1).

In addition, multidentate ligands such as shown in illustration (d) may be used

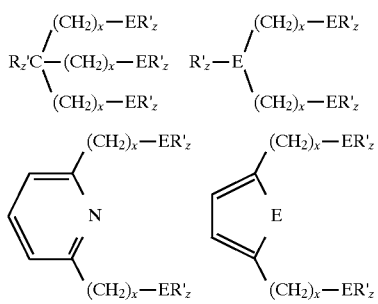 (d)

Representative (1) and (2) compounds include the following.

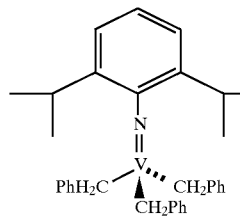

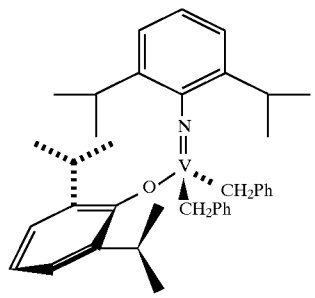

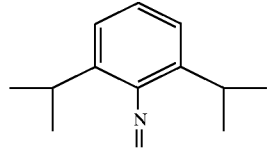

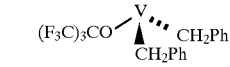

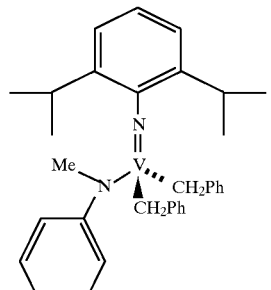

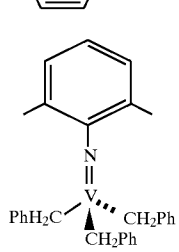

Representative (2) compounds include the following.

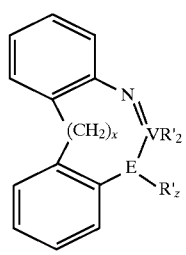

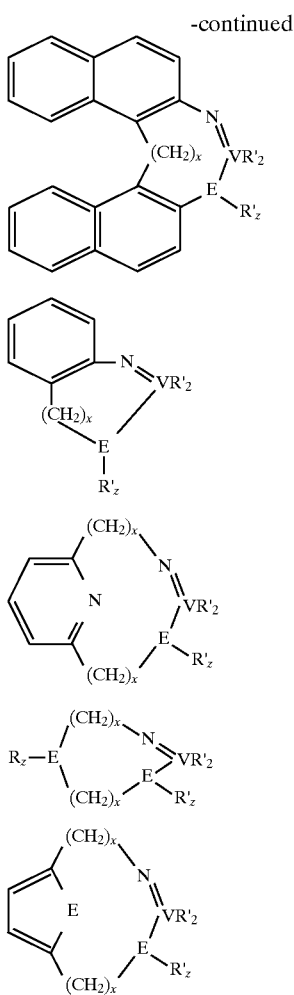

wherein E is either a Group 15 element (in which case z=1) or a Group 16 element (in which case z=1); x, R' is defined as above.

The catalyst compounds of the invention may be prepared in high yields using the following techniques. For vanadium, for example, the synthesis can begin with a reaction between vanadium oxytrichloride and a suitable organic molecule such as an isocyanate, an amine, or an alkali metal salt of an amine (See Scheme 1).

Scheme 1

$VOCl_3 + RNCO \rightarrow [RN]VCl_3$

Further chemical modifications can be made through ligand exchange reactions such as metathesis. (See Scheme 2).

Scheme 2

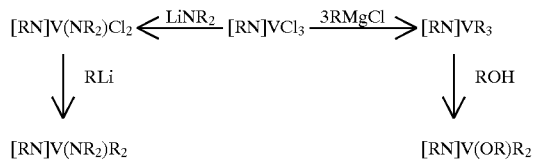

For instance, treatment of an arylimido-group (V) trialkyl complex with one equivalent of a protic reagent such as an amine or an alcohol, leads to elimination of one equivalent of alkane along with ligation of an amido group to form compounds of the invention. Alternatively the compounds of the invention may be prepared by initial substitution of a single chloride ligand from an arylimido-group (V) metal trichloride by reaction with, for example, an alkali metal salt of a alcohol, leading to the formation of an arylimido-group (V) metal (alkoxy) dichloride. Alkylation of the arylimido-group (V) (alkoxy) dichloride leads to formation of the compounds of the invention. A previous attempt to prepare compounds of these types has involved direct addition of alkylating agents to (tolylimido)vanadium (V) trichloride. This reaction led to the formation of (tolylimido)vanadium (V) (bis-methyltrimethylsilyl) chloride, see for example: Devore, D. D., J. Am. Chem. Soc., 1987, 109, 7408–7416. The methods described above for the preparation of the compounds of the invention offer greater versatility and control for steric and electronic variations around the metal center.

In addition, the use of (a) a low coordination number polyanionic ligand and (b) and an additional ancillary ligand which can donate lone pair π-electrons to the vanadium metal center (see representative examples of formula (2)) leads to enhanced stability thereby enabling the formation of vanadium alkyl complexes in which the vanadium metal center is stabilized in its highest oxidation state. This unexpected finding is corroborated by (1) the paucity of vanadium alkyl complexes in which the vanadium metal center is stabilized in its highest oxidation state and (2) reports confirming the instability of vanadium (V) alkyl complexes which do not possess the ancillary ligand arrangements of the compounds of the invention. For example, tert-butylimido-cyclopentadienyl vanadium dimethyl is reported to be thermally unstable, decomposing within minutes at room temperature. See Preuss, F. Z. Naturforsch 1990, 45b, 191–198.

Further details may be found in Progress in Inorganic Chemistry, Volume 42, 1994, 239–482, and other references readily available to those skilled in the art.

The Group 5 metal compounds according to the invention may be activated for polymerization catalysis in any manner sufficient to allow coordination or cationic polymerization. This can be achieved for coordination polymerization when one ligand can be abstracted and another will either allow insertion of the unsaturated monomers or will be similarly abstractable for replacement with a group that allows insertion of the unsaturated monomer, e.g., alkyl, silyl, or hydride. The traditional activators of coordination polymerization art are suitable, those typically include Lewis acids such as Ziegler organometallic cocatalysts and alumoxane compounds, and ionizing, anion precursor compounds that abstract one so as to ionize the Group 5 metal center into a cation and provide a counter-balancing noncoordinating anion.

The Ziegler cocatalyst will typically be a organometallic compound of a metal of Groups 1, 2, 12 or 13 of the Periodic table of elements. Preferred are organoaluminum compounds selected from the group consisting of aluminum alkyl, aluminum alkyl halide and aluminum halide. These can be represented by the formulae:

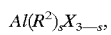
$Al(R^2)_s X_{3-s}$, wherein $R^2$ is independently a hydride or $C_1$ to $C_{10}$ hydrocarbyl radicals including aliphatic, alicyclic or aromatic hydrocarbon radicals, X is a halogen and s is an integer from 0 to 3; and, $Al_2R^2{}_3X_3$, which are hydrocarbylaluminum sesquihalides.

Examples include triethylaluminum, triisobutylaluminum, diethyl aluminumchloride, $Al_2Et_3Cl_3$ and $Al_2(i-BU)_3C_3$.

Alkylalumoxanes and modified alkylalumoxanes are suitable as catalyst activators, particularly for the invention metal compounds comprising halide ligands. The alumoxane component useful as catalyst activator typically is an oligomeric aluminum compound represented by the general formula $(R-Al-O)_n$, which is a cyclic compound, or $R(R-Al-O)_nAlR_2$, which is a linear compound. In the general alumoxane formula R is independently a $C_1$ to $C_{10}$ alkyl radical, for example, methyl, ethyl, propyl, butyl or pentyl and "n" is an integer from 1 to about 50. Most preferably, R is methyl and "n" is at least 4. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a mixture of the linear and cyclic species of the alumoxane. Methylalumoxane and modified methylalumoxanes are preferred. For further descriptions see, U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 Al, EP 0 279 586 B1, EP 0 516 476 A, EP 0 594 218 Al and WO 94/10180, each being incorporated by reference for purposes of U.S. patent practice.

When the activator is an alumoxane, the preferred transition metal compound to activator molar ratio is from 1:2000 to 10:1, more preferably from about 1:500 to 10:1, even more preferably from about 1:250 to 1:1 and most preferably from about 1:100 to 1:1.

The term "noncoordinating anion" is recognized to mean an anion which either does not coordinate to the metal cation or which is only weakly coordinated to it thereby remaining sufficiently labile to be displaced by a neutral Lewis base, such as an olefinically or acetylenically unsaturated monomer.

Descriptions of ionic catalysts, those comprising a transition metal cation and a noncoordinating anion, suitable for coordination polymerization appear in the early work in U.S. Pat. Nos. 5,064,802, 5,132,380, 5,198,401, 5,278,119, 5,321,106, 5,347,024, 5,408,017, 5,599,671, and international publications WO 92/00333 and WO 93/14132. These teach a preferred method of preparation wherein metallocenes are protonated by noncoordinating anion precursors such that an alkyl/hydride group is abstracted by protonation from a transition metal to make it both cationic and charge-balanced by the noncoordinating anion. Since the abstraction and insertion ligands of such metallocenes also may be ligands of the Group 5 metal compounds of the invention, similar methods of preparation as active polymerization catalyst components may be followed.

The use of ionizing ionic compounds not containing an active proton but capable of producing both the active Group 5 metal cation and an noncoordinating anion is also useful. See, EP-A-0 426 637, EP-A-0 573 403 and U.S. Pat. No. 5,387,568 for instructive ionic compounds. Reactive cations of the ionizing ionic compounds, other than the Bronsted acids, include ferrocenium, silver, tropylium, triphenylcarbenium and triethylsilylium, or alkali metal or alkaline earth metal cations such as sodium, magnesium or lithium cations.

A further class of noncoordinating anion precursors suitable in accordance with this invention are hydrated salts comprising the alkali metal or alkaline earth metal cations and a non-coordinating anion as described above. The hydrated salts can be prepared by reaction of the metal cation-noncoordinating anion salt with water, for example, by hydrolysis of the commercially available or readily synthesized $LiB(pfp)_4$ which yields $[Li \cdot xH_2O] [B(pfp)_4]$, where (pfp) is pentafluorophenyl or perfluorophenyl.

Any metal or metalloid capable of forming a coordination complex which is resistant to degradation by water (or other Bronsted or Lewis Acids) may be used or contained in the noncoordinating anion. Suitable metals include, but are not limited to, aluminum, gold, platinum and the like. Suitable metalloids include, but are not limited to, boron, phosphorus, silicon and the like. The description of noncoordinating anions and precursors thereto of the documents of the foregoing paragraphs are incorporated by reference for purposes of U.S. patent practice.

An additional method of making the active polymerization catalysts of this invention uses ionizing anion precursors which are initially neutral Lewis acids but form a Group 5 metal cation and the noncoordinating anion upon ionizing reaction with the invention compounds, for example tris(pentafluorophenyl) boron acts to abstract a hydrocarbyl, hydride or silyl ligand to yield a Group 5 metal cation and stabilizing noncoordinating anion, see EP-A -0 427 697 and EP-A-0 520 732 for illustration utilizing Group 4 metallocene compounds. See also the methods and compounds of EP-A-0 495 375. The description of noncoordinating anions and precursors thereto of these documents are similarly incorporated by reference for purposes of U.S. patent practice.

When the cation portion of an ionic noncoordinating anion precursor is a Bronsted acid such as protons or protonated Lewis bases (excluding water), or a reducible Lewis acid such as ferrocenium or silver cations, or alkaline metal or alkaline earth metal cations such as those of sodium, magnesium or lithium cations, the transition metal to activator molar ratio may be any ratio, but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred.

Thus suitable active catalyst complexes for coordination polymerization can be prepared by activation with the traditional metallocene activators, typically the alkylaluminum halides, alkylalumoxanes and ionizing boron or aluminum compounds known in the art. The active catalysts thus are catalytically active components comprising complexes derived from the Group 5 metal compounds containing the ancillary ligands according to the invention, and aluminum alkyls, alumoxanes or noncoordinating anions. The carbocationic catalyst complexes according to the invention will be those prepared with the ionizing noncoordinating anion precursor compounds.

The catalyst complexes of the invention are useful in polymerization of unsaturated monomers conventionally known to be polymerizable under either coordination polymerization conditions or cationic polymerization conditions using metallocenes. Such conditions are well known and include solution polymerization, slurry polymerization, and low, medium and high pressure gas-phase polymerization. The catalyst of the invention may be supported and as such will be particularly useful in the known operating modes employing fixed-bed, moving-bed, fluid-bed, or slurry processes conducted in single, series or parallel reactors.

When using the catalysts of the invention, particularly when immobilized on a support, the total catalyst system will generally additionally comprise one or more scavenging compounds. The term "scavenging compounds" as used in this application and its claims is meant to include those compounds effective for removing polar impurities from the reaction environment. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be used in the polymerization process itself.

Typically the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and n-octyl aluminum. Those scavenging compounds having bulky or $C_6$–$C_{20}$ linear hydrocarbyl substituents covalently bound to the metal or metalloid center being preferred to minimize adverse interaction with the active catalyst. Examples include triethylaluminum, but more preferably, bulky compounds such as triisobutylaluminum, trisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present will act as scavenger compounds and additional scavenging compounds may not be necessary. Alumoxanes also may be used in scavenging amounts with other means of activation, e.g., methylalumoxane and triisobutyl-aluminoxane. The amount of scavenging agent to be used with Group 5 catalyst compounds of the inventions is minimized during polymerization reactions to that amount effective to enhance activity and avoided altogether if the feeds can be sufficiently free of adventitious impurities.

The catalyst according to the invention may be supported for use in gas phase, bulk, slurry polymerization processes, or otherwise as needed. Numerous methods of support are known in the art for copolymerization processes for olefins, particularly for catalysts activated by alumoxanes, any is suitable for the invention process in its broadest scope. See, for example, U.S. Pat. Nos. 5,057,475 and 5,227,440. An example of supported ionic catalysts appears in WO 94/03056. A particularly effective method is that described in co-pending application U.S. Ser. No. 08/474,948 filed Jun. 7, 1995, and WO 96/04319. A bulk, or slurry, process utilizing supported, invention Group 5 metal compounds activated with alumoxane co-catalysts can be utilized as described for ethylene-propylene rubber in U.S. Pat. Nos. 5,001,205 and 5,229,478, these processes will additionally be suitable with the catalyst systems of this application. Both inorganic oxide and polymeric supports may be utilized in accordance with the knowledge in the field. See U.S. Pat. Nos. 5,422,325, 5,427,991, 5,498,582, 5,466,649, copending U.S. patent applications 08/265,532 and 08/265,533, both filed Jun. 24, 1995, and international publications WO 93/11172 and WO 94/07928. Each of the foregoing documents is incorporated by reference for purposes of U.S. patent practice.

In preferred embodiments of the process for this invention, the catalyst system is employed in liquid phase (solution, slurry, suspension, bulk phase or combinations thereof), in high pressure liquid or supercritical fluid phase, or in gas phase. Each of these processes may be employed in singular, parallel or series reactors. The liquid processes comprise contacting olefin monomers with the above described catalyst system in a suitable diluent or solvent and allowing said monomers to react for a sufficient time to produce the invention copolymers. Hydrocarbyl solvents are suitable, both aliphatic and aromatic, hexane and toluene are preferred. Halocarbon solvents, e.g., methylene chloride will additionally be suitable. Bulk and slurry processes are typically done by contacting the catalysts with a slurry of liquid monomer, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5,352,749, 5,436,304, 5,453,471, and 5,463,999, and WO 95/07942. Each is incorporated by reference for purposes of U.S. patent practice.

The use of alkyl halide promoters, such as hexachlorocyclopentadiene, ethyltrichloroacetate or benzoyl chloride with Ziegler vanadium catalysts to enhance performance (i.e., increase yields of polyethylene) is well known and may be used with the catalysts of this invention. See, for example, U.S. Pat. Nos. 4,232,140, 4,508,842, and EP-0 44 119 and EP-0 196 830, the descriptions of which are incorporated by reference for purposes of U.S. patent practice.

Generally speaking the polymerization reaction temperature can vary from about −50° C. to about 250° C. Preferably the reaction temperature conditions will be from −20° C. to 220°, more preferably below 200° C. The pressure can vary from about 1 mm Hg to 2500 bar, preferably from 0.1 bar to 1600 bar, most preferably from 1.0 to 500 bar. Where lower molecular weight copolymers, e.g., Mn<10,000, are sought it will be suitable to conduct the reaction processes at temperatures above about 0° C. and pressures under 500 bar. The multiboron activators of U.S. Pat. No. 5,278,119 can additionally be employed to facilitate the preparation of the low molecular weight copolymers of the invention.

Linear polyethylene, including high and ultra-high molecular weight polyethylenes, including both homo- and copolymers with other alpha-olefin monomers, alpha-olefinic and/or non-conjugated diolefins, for example, $C_3$–$C_{20}$ olefins, diolefins or cyclic olefins, are produced by adding ethylene, and optionally one or more of the other monomers, to a reaction vessel under low pressure (typically<50 bar), at a typical temperature of 20°–250 ° C. with the invention catalyst that has been slurried with a solvent, such as heptane or toluene. Heat of polymerization is typically removed by cooling. Gas phase polymerization can be conducted, for example, in a continuous fluid bed gas-phase reactor operated at 2000–3000 kPa and 60°–160° C., using hydrogen as a reaction modifier (100–200 ppm), $C_4$–$C_8$ comonomer feedstream (0.5–1.2 mol %), and $C_2$ feedstream (25–35 mol %). See, U.S. Pat. Nos. 4,543,399, 4,588,790, 5,028,670 and 5,405,922 and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between −10°–160° C. The process can be carried out in a stirred tank reactor, or more than one operated in series or parallel. See the general disclosure of U.S. Pat. No. 5,001,205 for general process conditions. See also, co-pending U.S. patent applications Ser. Nos. 08/426,363, filed Apr. 21, 1995 and 08/545,973 filed Oct. 20, 1995. All documents are incorporated by reference for description of polymerization processes, ionic activators and useful scavenging compounds.

Pre-polymerization of the supported catalyst of the invention may also be used for further control of polymer particle morphology in typical slurry or gas phase reaction processes in accordance with conventional teachings. For example such can be accomplished by pre-polymerizing a $C_2$–$C_6$ alpha-olefin for a limited time, for example, ethylene is contacted with the supported catalyst at a temperature of −15° to 30° C. and ethylene pressure of up to about 250 psig (1724 kPa) for 75 min. to obtain a polymeric coating on the support of polyethylene of 30,000–150,000 molecular weight. The pre-polymerized catalyst is then available for use in the polymerization processes referred to above. The use of polymeric resins as a support coating may additionally be utilized, typically by suspending a solid support in dissolved resin of such material as polystyrene with subsequent separation and drying. All documents are incorporated by reference for description of metallocene compounds, ionic activators and useful scavenging compounds.

Other olefinically unsaturated monomers besides those specifically described above may be polymerized using the catalysts according to the invention either by coordination or carbocationic polymerization, for example, styrene, alkyl-substituted styrene, ethylidene norbornene, norbornadiene, dicyclopentadiene, and other olefinically-unsaturated monomers, including other cyclic olefins, such as cyclopentene, norbornene, alkyl-substituted norbornenes, and including isobutylene, isoprene, butadiene, vinyl ethers, vinyl carbazoles, etc. Additionally, alpha-olefinic macromonomers of up to 100 mer units, or more, may also be incorporated by copolymerization.

Lubricating oil additive compositions can be prepared advantageously when low molecular weight alpha-olefin copolymers having vinyl or vinylidene terminal unsaturation are prepared with the catalysts of the invention. See the disclosures of U.S. Pat. No. 5,498,809 and international patent applications WO 93/24359, WO 94/19436 and WO 94/13715 and documents listed therein for further information as to low molecular weight alpha-olefin polymers. Each is incorporated by reference for purposes of U.S. patent practice.

In a similar manner, but utilizing higher molecular weight (10,000<Mn<300,000) alpha-olefin/diolefin copolymer having a crystallinity low enough to permit of oil solubility (e.g., <40% crystallinity), as in copending U.S. applications Ser. No. 08/426,363, filed Apr. 21, 1995, and 08/545,973, filed Oct. 20, 1995, multifunctional viscosity modifying lubricating oil additives can be produced. See the descriptions of lubricating oil modifiers and lubricating oil compositions in U.S. Pat. Nos. 4,749,505, 4,772,406 and WO-A-93/12148, all incorporated by reference for purposes of U.S. patent practice.

Carbocationic polymerization can be effected by use of the catalysts of the invention when converted to active cationic species by activating ionization. Such polymerization techniques are well known in the art, see Kennedy, J. P., *Carbocationic Polymerization of Olefins:A Critical Inventory* (John Wiley & Sons, 1975). See also, Baird, Michael C., et al, $\eta^5$-$C_5Me_5TiMe_3B(C_6F_5)_3$: A Carbocationic Olefin Polymerization Initiator Masquerading as a Ziegler-Natta Catalyst, J. Am. Chem. Soc. 1994, 116, 6435–6436, for conditions under which the first row metal Ti in stable metallocene cationic form was used for carbocationic polymerization. Each is incorporated by reference for purposes of U.S. patent practice.

The catalyst compositions of the invention can be used as described above individually for coordination or carbocationic polymerization or can be mixed to prepare polymer blends with other known olefin polymerization catalyst compounds. By selection of monomers, blends of coordination catalyst compounds or blends of carbocationic catalyst compounds, or any together, polymer blends can be prepared under polymerization conditions analogous to those using individual catalyst compositions. Polymers having increased MWD for improved processing and other traditional benefits available from polymers made with mixed catalyst systems can thus be achieved.

The following examples are presented to illustrate the foregoing discussion. All parts, proportions and percentages are by weight unless otherwise indicated. Ambient temperatures were used for the polymerization examples unless otherwise noted. Although the examples may be directed to certain embodiments of the present invention, they are not to be viewed as limiting the invention in any specific respect. In these examples certain abbreviations are used to facilitate the description. These include standard chemical abbreviations for the elements and certain commonly accepted abbreviations, such as:Me=methyl, Et=ethyl, $Pr^i$=isopropyl, Bu=butyl, Ph=phenyl, and THF=tetrahydrofuran.

Example 1—Catalyst Preparation (a) Preparation of $(2,6-Pr^i_2C_6H_3N)VCl_3 \cdot THF$ A solution of 25 g of $VOCl_3$ (0.14 mol) and 25 g 2,6-diisopropylphenylisocyanate (0.12 mol) in 100 ml. octane were refluxed for 24 hours. Subsequent solvent removal under reduced pressure yielded a dark green oily solid. This solid was extracted with 50 mL of pentane, filtered and treated with approximately 20 mL of THF to produce a sandy colored precipitate. Collection by filtration yielded 33.6 g of $(2,6-Pr^i_2C_6H_3N)VCl_3 \cdot THF$. A further 6.0 g was obtained by a second extraction of the remaining green oily solid, subsequent treatment with THF and isolation by filtration. Total yield 39.6 g (0.10 Mol), 69% based on vanadium.

(b) Preparation of $(2,6-Pr^i_2C_6H_3N)V(CH_2C_6H_5)_3$

A solution of $(2,6-Pr^i_2C_6H_3N)VCl_3 \cdot THF$ (20 g, 0.049 mol) in 50 mL hexane was cooled to −30° C. A solution of $C_6H_5CH_2MgCl$ (148 mL, 1M solution in diethylether, 0.148 mol) was added dropwise over a period of 15 minutes leading to a change in the color of the solution from green to red. The resultant red solution was allowed to warm up to room temperature whereupon it was filtered and the solvent removed under a stream of nitrogen. Recrystallization of the resultant crude oily solid from hexane yielded $(2,6-Pr^i_2C_6H_3N)V(CH_2C_6H_5)_3$ as a dark red crystalline solid (16 g, 0.032 mol, 65%).

(c) Preparation of $(2,6-Pr^i_2C_6H_3N)V(OC(CF_3)_3)(CH_2C_6H_5)_2$

A solution of $(2,6-Pr^i_2C_6H_3N)V(CH_2C_6H_5)_3$ (0.53 g, 1.0 mmol) in 20 mL hexane was treated with $(CF_3)_3COH$ (138 μL, 1.0 mmol) and stirred overnight. Solvent removal under a stream of nitrogen left an oily brown solid. Recrystallization from a hexane solution at −30° C. produced large dark brown crystals of $(2,6-Pr^i_2C_6H_3N)V(OC(CF_3)_3)$ $(CH_2C_6H_5)_2$ in 60% yield (0.40 g, 0.6 mmol).

(d) Preparation of $(2,6-Pr^i_2C_6H_3N)V(NPhMe)(CH_2C_6H_5)_2$

A solution of $(2,6-Pr^i_2C_6H_3N)V(CH_2C_6H_5)_3$ (0.3 g, 0.6 mmol) in 20 mL hexane was treated with N-methylaniline (65 μL, 0.6 mmol) and stirred for 48 hours. Solvent removal under a stream of nitrogen left an oily brown solid. Recrystallization from a hexane solution at −30° C. produced red crystals of $(2,6-Pr^1_2C_6H_3N)V(NPhMe)(CH_2C_6H_5)_2$ in 55% yield (0.17 g, 0.33 mmol).

(e) Preparation of $(2,6-Pr^i_2C_6H_3N)V(OC_6H_{3-2,6}-Pr^i_2)(CH_2C_6H_5)_2$

A solution of $(2,6-Pr_{i2}C_6H_3N)V(CH_2C_6H_5)_3$ (1.2g, 2.4 mmol) in 20 mL dichloromethane was treated with $2,6-Pr^i_2C_6H_3OH$ (450 μL, 2.4 mmol) and stirred for 48 hours. Solvent removal under a stream of nitrogen left an oily red-brown solid. Recrystallization from a hexane solution at −30° C. produced dark red crystals of $(2,6-Pr^i_2C_6H_3N)V(OC_6H_3-2,6-Pr^1_2)(CH_2C_6H_5)_2$ in 75% yield (1.05 g, 1.8 mmol).

(f) Preparation of $(2,6-Me_2-C_6H_3N)V(CH_2C_6H_5)_3$

A solution of $(2,6-Me_2-C_6H_3N)VCl_3\cdot THF$ (0.50 g, 1.4 mmol) in 20 mL of hexane was cooled to −30° C. A solution of $C_6H_5CH_2MgCl$ (4.3 mL, 1M solution in diethylether, 4.3 mmol) was added dropwise over a period of 15 mins leading to a change in the color of the solution from green to red. The resultant red solution was allowed to warm up to room temperature whereupon it was filtered and the solvent removed under a stream of nitrogen. Recrystallization of the resultant crude oily solid from hexane yielded $(2,6-Me_2C_6H_3N)V(CH_2C_6H_5)_3$ as a dark red crystal g, 0.6 mmol, 40%).

Example 2—Polymerization Examples (a) A catalyst solution containing 10 mg $(2,6-Pr^i_2-C_6H_3N)V(CH_2C_6H_5)_3$ and 10 mg $B(C_6F_5)_3$ was prepared in 3 mL of toluene. The catalyst solution, along with 400 mL of hexane, and 45 mL 1-hexene was added to a 1 liter stainless-steel autoclave which had been previously purged with nitrogen. The autoclave was pressurized with ethylene at 150 psi and the mixture was stirred at 30° C. for 1 hour whereupon the autoclave was vented. 4.6 g of polymer was produced using this procedure.

(b) A catalyst solution containing 50 mg $(2,6-Pr^i_2-C_6H_3N)V(NPhMe)(CH_2C_6H_5)_2$ and 80 mg $[PhNHMe_2][B(C_6F_5)_4]$ was prepared in 5 mL of toluene in a serum capped bottle. Ethylene was bubbled through the solution for 10 minutes causing the precipitation of polymer. The bottle was opened and the contents diluted with water. The solid polymer was washed with acetone and dried. The yield of polyethylene was 1 g.

(c) A catalyst solution containing 10 mg $(2,6-Pr^i_2-C_6H_3N)V(OC(CF_3)_3)(CH_2C_6H_5)_2$ in 5 mL of toluene was treated with 5 mL of a solution containing 10 wt % methylalumoxane. The catalyst solution, along with 400 mL of hexane and 45mL 1-hexene was added to a 1 liter stainless-steel autoclave which had been previously purged with nitrogen. The autoclave was pressurized with ethylene at 100 psi and the mixture was stirred at 25° C. for 1 hour whereupon the autoclave was vented. 7.5 g of polymer was produced from this procedure.

(d) A catalyst solution containing 50 mg $(2,6-Pr^i_2-C_6H_3N)V(OC_6H_3-2,6-Pr^i_2)(CH_2C_6H_5)_2$ and 78 mg $[Ph_3C][B(C_6F_5)_4]$ was prepared in 5 mL of toluene. The catalyst solution, along with 400 mL of hexane and 45 mL 1-hexene was added to a 1 liter stainless-steel autoclave which had been previously purged with nitrogen. The autoclave was pressurized with ethylene at 150 psi and the mixture was stirred at 30° C. for 1 hour whereupon the autoclave was vented. 1 g of polymer was produced from this procedure.

(e) In this example a mixture of 20 mg $(2,6-Me_2-C_6H_3N)V(CH_2C_6H_5)_3$ and 25 mg $[PhNHMe_2][B(C_6F_5)_4]$ was prepared in 5 mL of toluene. 10 mL 1-hexene was then added to the resultant mixture. After 1 hour the solvent was removed under a stream of nitrogen and the solid polymer was washed with acetone and dried. The yield of polyhexene was 1 g.

We claim:

1. An olefin polymerization catalyst composition comprising the reaction product of:

1) a Group 5 metal compound stabilized in its highest metal oxidation state comprising one Group 15 element polyanionic ancillary ligand and three single or multidentate univalent ligands comprising Group 14–16 elements bound to the Group 5 metal, but excluding cyclopentadienyl ligands wherein at least one of said univalent ligands comprises a Group 14 element bound to the Group 5 metal, and 2) a catalyst activator compound.

2. The catalyst composition of claim 1 wherein said univalent ligands comprise one ligand comprising a Group 15–16 element and two ligands comprising Group 14 elements, said elements bound to the Group 5 metal. element, n=1 when X is covalently linked to R and n=0 when X is not covalently linked to R.

3. The catalyst composition of claim 1 wherein said Group 5 metal compounds are represented by the symbols:

(1) $[RJ]MR'_3$, and (2) $[(RJ)Z_n(Q)]MR'_2$ where M is a Group 5 transition metal; J is a Group 15 heteroatom ligand covalently bound to M; R is a substituted or unsubstituted aryl, hydrocarbyl or organometalloid group covalently bound to J; each R' is, independently, a uninegative ligand selected from the group consisting of substituted or unsubstituted aryl, substituted or unsubstituted linear or cyclic hydrocarbyl, silyl, hydride or substituted or unsubstituted organometalloid group; Q is a univalent single or multidentate ancillary ligand comprising at least one Group 14–16 element covalently bound to M; and, Z is an optional covalent bridging group linking R and Q, comprising at least one Group 14–16 element, n=1when Q is covalently linked to R and n=0 when Q is not covalently linked to R.

4. The catalyst composition of claim 1 wherein said Group 5 metal is vanadium.

5. The catalyst composition of claim 3 wherein said Group 5 metal is vanadium.

6. The catalyst composition of claim 4 wherein compound 1) is selected from the group consisting of $(2,6-Pr^i_2C_6H_3N)V(CH_2C_6H_5)_3$, $(2,6-Pr^i_2C_6H_3N)V(OC(CF_3)_3)(CH_2C_6H_5)_2$, $(2,6-Pr^i_2C_6H_3N)V(NPhMe)(CH_2C_6H_5)_2$, $(2,6-Pr_{i2}C_6H_3N)V(OC_6H_3-2,6-Pr^i_2)(CH_2C_6H_5)_2$, and $(2,6-Me_2C_6H_3N)V(CH_2C_6H_5)_3$.

7. The catalyst composition of claim 1 wherein said catalyst activator compound is an alkylalumoxane or an aluminum alkyl.

8. The catalyst composition of claim 1 wherein said catalyst activator compound is an ionizing noncoordinating anion precursor compound.

* * * * *